(12) United States Patent
Cherkes

(10) Patent No.: US 6,663,765 B2
(45) Date of Patent: Dec. 16, 2003

(54) METHOD AND DEVICE FOR THE MANUFACTURE OF THE MEDICAL EXPANDING STENTS

(76) Inventor: David Cherkes, Jabotinsky St. 6/4, Tveria (IL)

( * ) Notice: Subject to any disclaimer, the term of this patent is extended or adjusted under 35 U.S.C. 154(b) by 30 days.

(21) Appl. No.: 09/950,659

(22) Filed: Sep. 13, 2001

(65) Prior Publication Data

US 2002/0023843 A1 Feb. 28, 2002

Related U.S. Application Data

(63) Continuation-in-part of application No. 09/616,060, filed on Jul. 13, 2000, now abandoned.

(51) Int. Cl.[7] .................................................. B23H 3/00
(52) U.S. Cl. ...................... 205/668; 205/640; 205/672; 205/686; 204/212; 204/224 R; 204/224 M; 204/275.1; 204/297.1; 204/297.06; 128/898; 623/1.2; 623/901; 623/902; 623/903; 623/909
(58) Field of Search ................................ 204/194, 212, 204/224 R, 224 M, 228.7, 228.8, 297.01, 297.06, 275.1; 205/67, 73, 75, 640, 641, 646, 648, 649, 651, 652, 654, 662, 663, 668, 672, 686; 606/198; 623/1.2, 901, 902, 903, 909; 128/898

(56) References Cited

U.S. PATENT DOCUMENTS

| | | | |
|---|---|---|---|
| 3,567,897 A | * 3/1971 | Inoue | 219/71 |
| 4,383,896 A | 5/1983 | Pruyn et al. | 204/11 |
| 4,496,434 A | 1/1985 | Morssinkhof | 204/11 |
| 4,733,665 A | 3/1988 | Palmaz | 128/343 |
| 4,776,337 A | 10/1988 | Palmaz | 128/343 |
| 4,856,516 A | 8/1989 | Hillstead | 128/343 |
| 4,907,336 A | 3/1990 | Gianturco | 29/515 |
| 5,030,329 A | 7/1991 | Haidle et al. | 204/9 |
| 5,116,365 A | 5/1992 | Hillstead | 623/1 |
| 5,135,536 A | 8/1992 | Hillstead | 606/195 |
| 5,328,587 A | 7/1994 | Fenske | 205/73 |
| 5,421,955 A | 6/1995 | Lau et al. | 216/48 |
| 5,514,154 A | 5/1996 | Lau et al. | 606/195 |
| 5,649,952 A | * 7/1997 | Lam | 623/1.15 |
| 5,707,386 A | 1/1998 | Schnepp-Pesch et al. | 606/194 |
| 5,725,548 A | 3/1998 | Jayaraman | 606/198 |
| 5,772,864 A | 6/1998 | Moller et al. | 205/73 |
| 5,902,475 A | 5/1999 | Trozera et al. | 205/655 |
| 5,907,893 A | 6/1999 | Zadno-Azizi et al. | 29/6.1 |
| 6,117,165 A | * 9/2000 | Becker | 623/1.15 |
| 6,375,826 B1 | * 4/2002 | Wang et al. | 205/684 |
| 2001/0039449 A1 | * 11/2001 | Johnson et al. | 623/1.19 |

* cited by examiner

*Primary Examiner*—Nam Nguyen
*Assistant Examiner*—Brian L Mutschler
(74) *Attorney, Agent, or Firm*—Blank Rome LLP

(57) ABSTRACT

Method and device for manufacturing of expandable cylindrical metal meshes for use in expandable stents and in particular for customized manufacturing. The method includes determining the type and size of the stent to be implanted, electrochemically forming the stent with desired pattern of meshes and implanting the stent into patient. The method comprises using a cathode with desired pattern of meshes and a tubular blank, from which the stent is formed. Between the cathode and the blank is delivered an electrolyte and the cathode and the blank are simultaneously rotated during electrochemical forming process.

40 Claims, 14 Drawing Sheets

METHOD AND DEVICE FOR THE MANUFACTURE OF THE MEDICAL EXPANDING STENTS

This application is a continuation-in-part of Ser. No. 09/616,060 filed Jul. 13, 2000 now abandoned.

FIELD OF THE INVENTION

The invention relates to the manufacture of expandable cylindrical metal meshes for use in expandable stents and in particular to the customized manufacture of expandable metal stents.

BACKGROUND OF THE INVENTION

A cardiologist performing a stent implant procedure requires several stents of various geometrical shapes and lengths in order to be able to quickly choose an optimal stent during the surgery. Depending on the location and degree of damage being repaired, the cardiologist may need as many as eight different pattern stents with lengths ranging from about 6 mm to about 40 mm. During surgery, the cardiologist may have as little as five minutes to select the proper stent. Therefore, hospitals and clinics performing these procedures generally have a substantial number of stents on hand, perhaps as many as 40 or more, for use with a single patient. Given the relatively high cost of stents and their consumption, hospital and clinic expenditures on such operations may be substantial. As a result, many hospitals and clinics without adequate financial resources do not perform surgical procedures involving stent implantation.

There exists, therefore, a need for a system that reduces the number of costly stents required during surgical procedures by allowing a surgeon or clinic staff to select and fabricate a custom stent during a surgical procedure and within a short period of time.

Methods that have previously been used to manufacture stents are described in U.S. Pat. Nos. 4,856,516, 4,907,336, 5,116,365, 5,135,536, and 5,707,386. Stents produced by the methods disclosed therein contain bent wires that are knotted, which introduces stresses into the metal and decreases the quality of the stents. Moreover, these stents are not generally suitable for curved portions of blood vessels. More importantly, these methods only produce stents with a configuration that is tailored to a specific surgical instrument, limiting their usefulness. Other methods that have been used to manufacture stents are described in U.S. Pat. Nos. 5,725,548 and 5,907,893. Stents produced by the methods disclosed therein are joined along a line longitudinal to the length of the stent and then welded. However, at the high temperatures required to weld these joints, the crystalline structure of the metal can be affected and thereby reduce the reliability and strength of the stent and its compatibility in a biochemical environment.

Still other methods of manufacturing stents are described in U.S. Pat. Nos. 4,383,896, 4,496,434, 5,030,329, 5,328,587 and 5,772,864. Stents produced by the methods disclosed therein are free from wire knots and welded joints. They are produced using an electrochemical process, which generally produces higher quality stents. However, the methods disclosed, most notably in U.S. Pat. No. 5,772,864, are complex and time consuming. For example, grooves outlining the stent must be etched on very small mandrels with instruments requiring precise control. Then, the cleaned mandrel must be dipped in an electrochemical bath containing a selected metal for up to approximately 12 hours. The stent material must then be carefully removed and further processed and polished. Because the entire process is costly and time consuming, it is not appropriate for use in a hospital or clinical setting during a shunting procedure.

Still other methods of manufacturing stents are described in U.S. Pat. Nos. 4,733,665, 4,776,337, 5,421,955 and 5,514,154. Stents produced by the methods disclosed therein are made using laser technology to directly carve the geometrical contours of stents on tubular blanks. Manufacturing of stents by these methods is associated with formation of sharp edges and burrs on the outside and inside surface of the stent. This can affect the structure of the stent, thereby reducing its reliability. This also requires additional processing to remove these undesirable features. Moreover, the cost and complexity of this technology can limit its use in hospital and clinical settings.

A solution to some of these problems is disclosed in U.S. Pat. No. 5,421,955, where laser technology is used to form a pattern on a mask material that is subsequently etched in an electrochemical process. However, this process requires complex instruments for precise laser control, an etching bath and solution, and extended processing time that may prohibit its use in a hospital or clinical setting.

A proposed solution to the above mentioned problems is disclosed in U.S. Pat. No. 5,902,475 in which much of the stent processing may be carried out prior to its use in a surgical procedure, with the final processing done in the hospital or clinical setting. For example, a tubular blank is coated with a photoresistive polymer over a photo film that contains a stent pattern. It is mounted on a rotatable tube and exposed to ultraviolet rays, thereby creating a negative image of the stent. The film is developed such that the illuminated lines solidify. The film is then placed in an electrochemical bath and the non-illuminated surfaces dissolve. The steps of blank mounting and removing can require up to a total of approximately six minutes to accomplish. The step of transferring and immersing the blank in the electrochemical tank can require up to approximately ten minutes. The step of electrochemically removing the non-illuminated areas can require up to approximately six minutes, with the final step of polishing/processing taking up to approximately 3 minutes. In total, the process described in U.S. Pat. No. 5,902,475 takes about thirty minutes, limiting its usefulness during surgical procedures. Moreover, this process requires, for certain applications, use of cathode made from platinum, gold or their alloys to withstand the strong acidic electrolyte solutions, phosphoric or sulfuric acid. Additional processing steps to prepare the stent for subsequent use may also be required. It is apparent that the additional expense and hazards associated with this method prohibit its use in hospital or clinical settings.

Stents produced by the methods described in U.S. Pat. Nos. 5,421,955, 5,772,864 and 5,902,475 rely on technology that prevents production of high quality stents. For example, the inner surface structure of the holes in the base stent tubes may be nonhomogeneous after the electrochemical treatment, e.g., includes sharp edges, protrusions, etc. Under certain conditions, the stent blank could become contaminated with impurities such as oxides or include other defects. Under these conditions, current supplied to the blank during processing would not be uniform. Further, an additional step is required to process the inner surface of the stent holes. Therefore, it would be desirable to apply the electric current to the external surface of the stent blank during processing rather than the inner surface.

Additionally, the known manufacturing methods may require the use of a diamond dust polishing tool to treat not only the external surface of the final stent but also the internal surface area. This additional step adds to the cost and complexity of the manufactured stent.

Accordingly, prior to the present invention, there have been no described methods of manufacturing stents: that allow surgical or clinical staff to fabricate custom stents as an integral part of the surgical procedure; that require relatively few complicated instruments or dangerous chemicals, that is relatively inexpensive; and that produces stents free from thermal stresses, sharp edges or surface irregularities.

SUMMARY OF THE INVENTION

In accordance with the present invention, a method and device for manufacturing and implanting an expandable stent into a body lumen is carried out by electrochemically forming the expandable stent just prior to implantation. The electrochemical forming includes providing a cathode which includes a pattern for producing the stent; providing a tubular blank adjacent to the cathode; delivering an electrolyte between the cathode and the tubular blank; relative displacing the tubular blank and the cathode; and, electrochemically producing the stent with the stent pattern for subsequent implantation.

Other features of the invention include using a tubular blank that has a diameter and thickness equal to the stent to be manufactured; cutting the ends of the tubular blank after the stent outline is formed; using a mandrel for receiving the tubular blank, in which the mandrel has a linear slit along its longitudinal length parallel to the tubular blank for the introduction of electrolyte and wherein the linear slit is narrower than the diameter of the tubular blank; removing an insulating coating on the cathode before electrochemically forming the stent; customizing the expandable stent according to the needs of a patient being treated; and implanting the stent into a body lumen.

Still other features include electrochemically forming at a current density of about range 50 A/cm$^2$, or more; delivering the electrolyte at a velocity of from 8 m/s to 10 m/s; and displacing the blank by centerless rotation.

Also disclosed in a method of custom-forming an expandable stent in an operating or emergency room during a procedure to implant the stent into a body lumen of a patient, including providing a plurality of cathodes, at least some of which includes a different stent pattern, mounting the cathodes on a rotator; providing a plurality of tubular blanks, at least some of which includes a different material, diameter and thickness; selecting working cathode with a desired stent pattern; selecting a stent blank from the plurality of tubular blanks; mounting the stent blank in an operative relationship to the working cathode; rotating the rotator while delivering an electrolyte between the desired stent pattern and the stent blank to electrochemically form the stent having the desired stent pattern; and recovering and preparing the recovered stent for implantation into the patient's body lumen.

Other features of the invention include using a mandrel for receiving the stent blank, in which the mandrel has a linear slit along its longitudinal length parallel to the stent blank for the introduction of electrolyte and wherein the linear slit is narrower than the diameter of the stent blank; removing an insulating coating on the plurality of cathodes before electrochemically forming the stent; electrochemical forming at a current density of about range 50 A/cm$^2$, or more; cutting the ends of the electrochemically-formed stent outline; delivering the electrolyte at a velocity of from 8 m/s to 10 m/s; and rotating the tubular blank by centerless rotation.

Also disclosed is an apparatus for custom-forming an expandable stent in an operating or emergency room during a procedure to implant the stent into a body lumen of a patient for implantation into a body lumen, which includes a rotator, for carrying one or more cathodes; a mandrel positioned parallel to the rotational axis of the rotator, for holding a tubular blank in operative relationship to the working cathode which is currently employed for custom forming; a conduit for delivering electrolyte to the working cathode and the tubular blank; means for simultaneously rotating the rotator and the tubular blank; and means for supplying electrical voltage to the working cathode and to the tubular blank to produce a stent.

Other features of the apparatus aspects of the invention may include a grinding means for removing an insulating coating from the cathodes; means for separating the working cathode with the desired stent pattern and the tubular blank by a distance of not more than 0.05 mm; a mandrel with a linear slit directed parallel to the length of the tubular blank for the delivery of the electrolyte between the working cathode and the tubular blank and wherein the linear slit is narrower than the diameter of the tubular blank; one or more cathodes being made from a metal selected from the group consisting of gold, platinum, stainless steel, brass, copper, or alloys thereof; and a tubular blank that has a diameter and thickness equal to the stent.

Another feature of the invention include a housing for containing therein the mandrel, the rotator, the tubular blank, the one or more cathodes, and the conduit and wherein the housing is positionable in an area substantially near a patient being treated for a stent implant.

Still other features of the invention include a lateral support comprising two pairs of tubular rests, the pairs of tubular rests each containing longitudinal slits, for supporting the tubular blank in the mandrel in an operative relationship to the working cathode, and a means for self-aligning the mandrel in operative relationship to the working cathode.

These and other objects, advantages and features of the invention will become better understood from a detailed description of the preferred embodiment of the invention, which is described in conjunction with the accompanying drawings.

DETAILED DESCRIPTION OF THE PREFERRED EMBODIMENT

Figure 1:
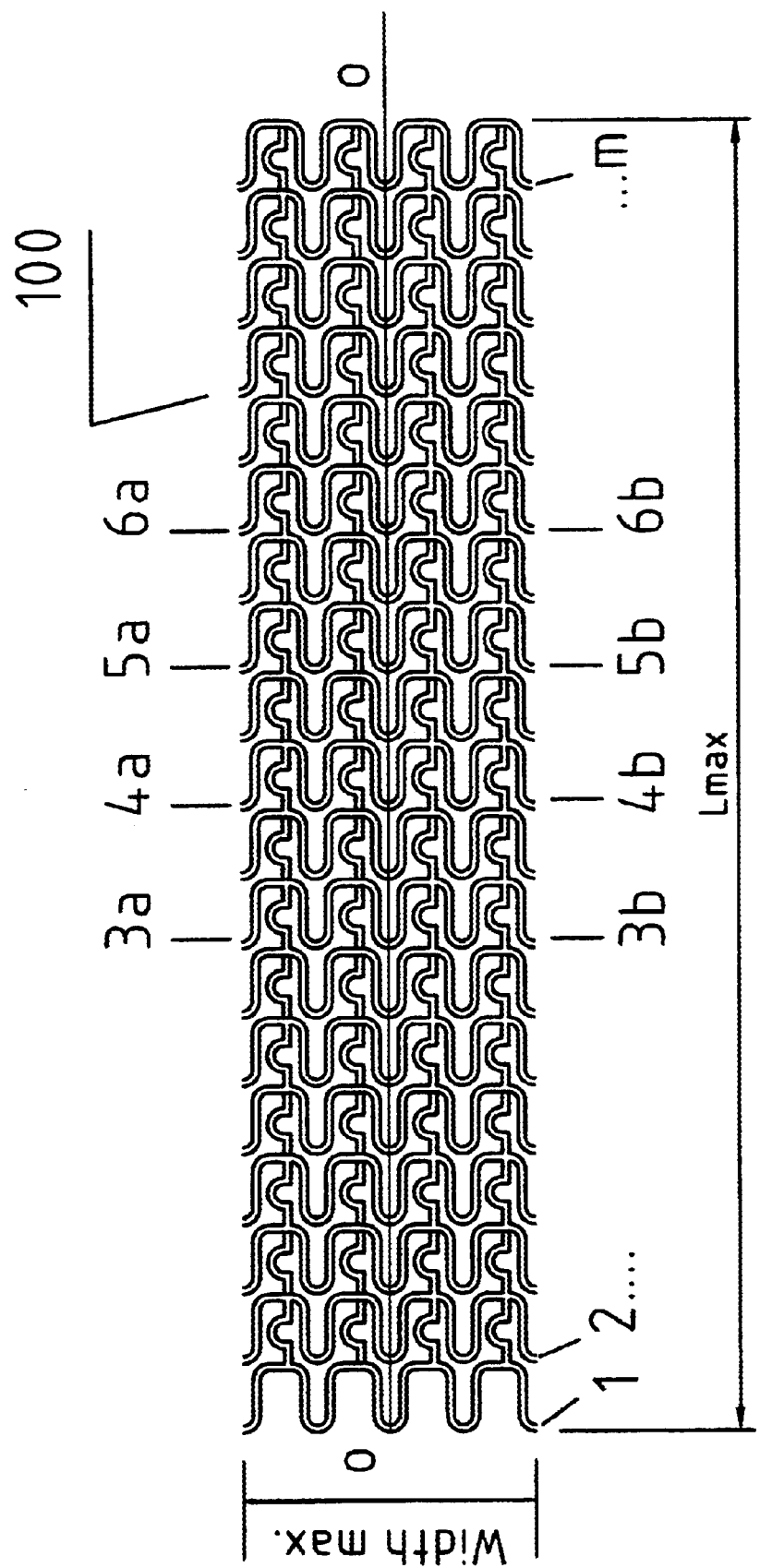
FIG. 1 is a schematic of a geometric pattern for a stent manufactured in accordance with the present invention.

FIG. 1 shows flat development of a cylindrical stent with an example of the pattern of an individual stent 100 manufactured in accordance with the present invention. The development of the stent 100 has a maximum length dimension, Lmax, and a maximum width dimension, which may be about 6.28 mm or wider. Shorter stent lengths may be produced by cutting along lines 3a–3b, 4a–4b, or along any other line perpendicular to the length dimension of the stent.

Figure 5:
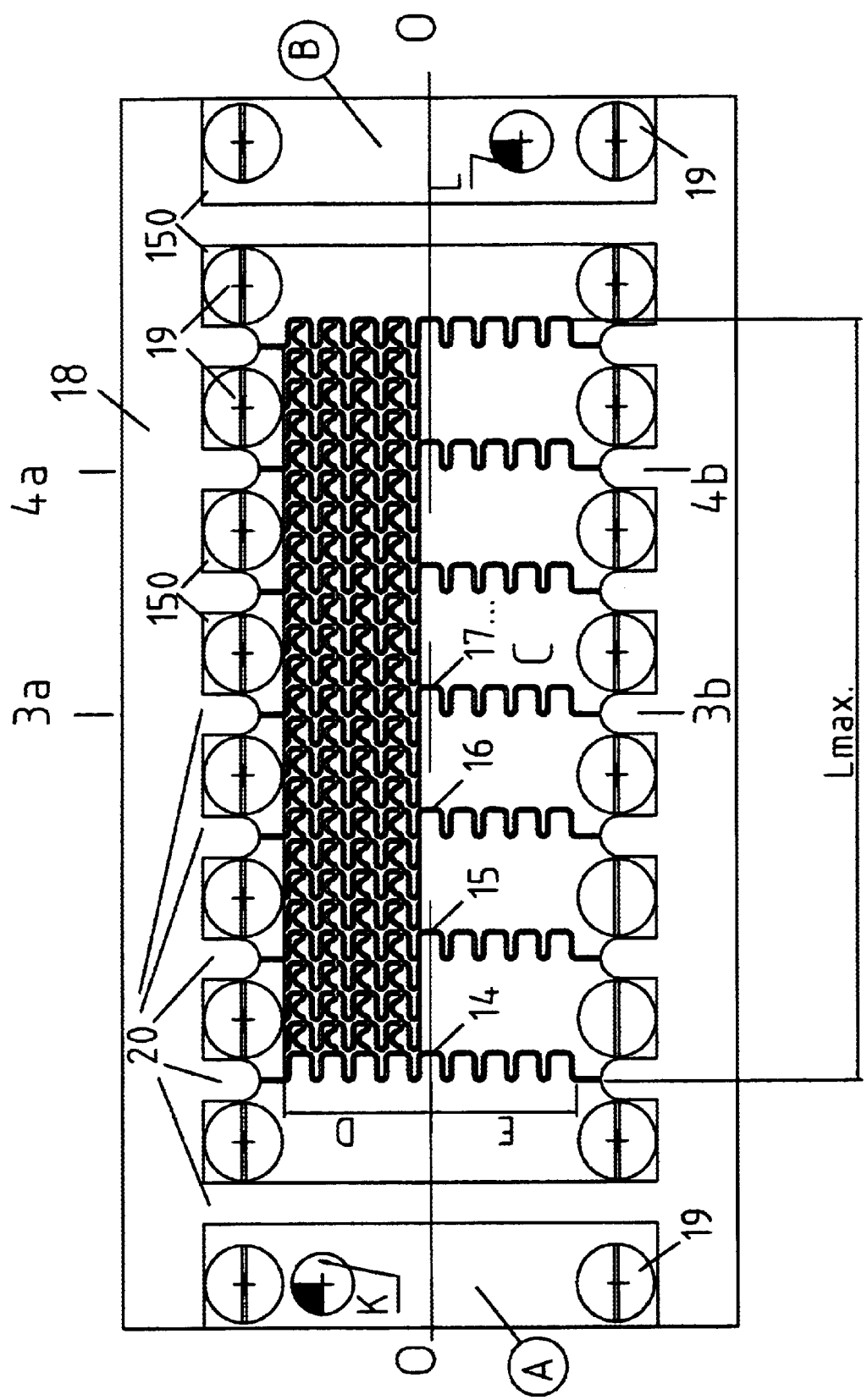
FIG. 5 is a schematic depicting the top view of a single cathode manufactured in accordance with the present invention.

The stent 100 is prepared first by forming an outline of the stent 100 on a rounded or flat surface of a cathode metal plate 150 (FIG. 5). The material of the cathode may be gold, platinum, or alloys of the same, or stainless steel, brass or other copper alloys. The outline is created using one or more etching, drilling, photochemical, electroerosion or other process steps known in the prior art.

Figure 2:
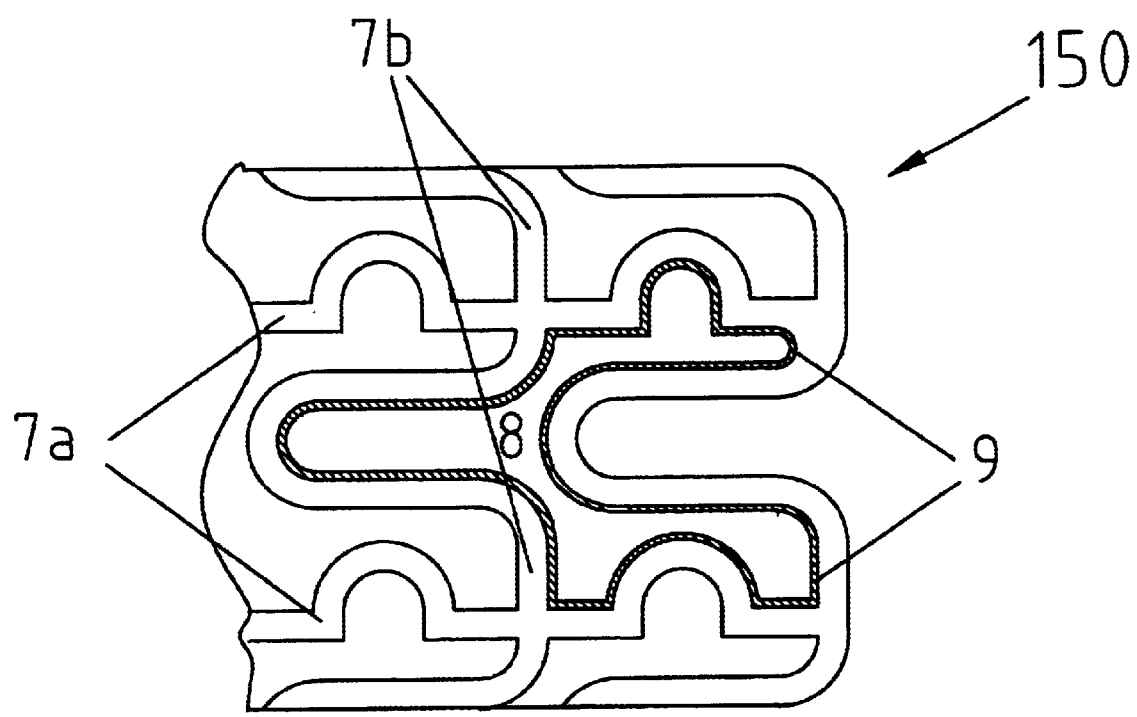
FIG. 2 is a detailed schematic of one cell of a cathode used for making the stent in accordance with the present invention.

FIG. 2 shows the result of this outlining step and the formation of individual stent cells defined by, stent bridges 7a, 7b and depressions 8 on the cathode metal plate. The bridges and depressions are made by removing material of cathode 150 at a depth of up to about 0.2 mm. This results in the formation of the outline band 9, corresponding to the outline pattern of the stent 100. This outline band after removal of the cathode material becomes a raised portion of the cathode metal plate 150. The remaining lowered portions of the plate are filled with an insulating material, e.g. self-hardening resin.

Figure 3:
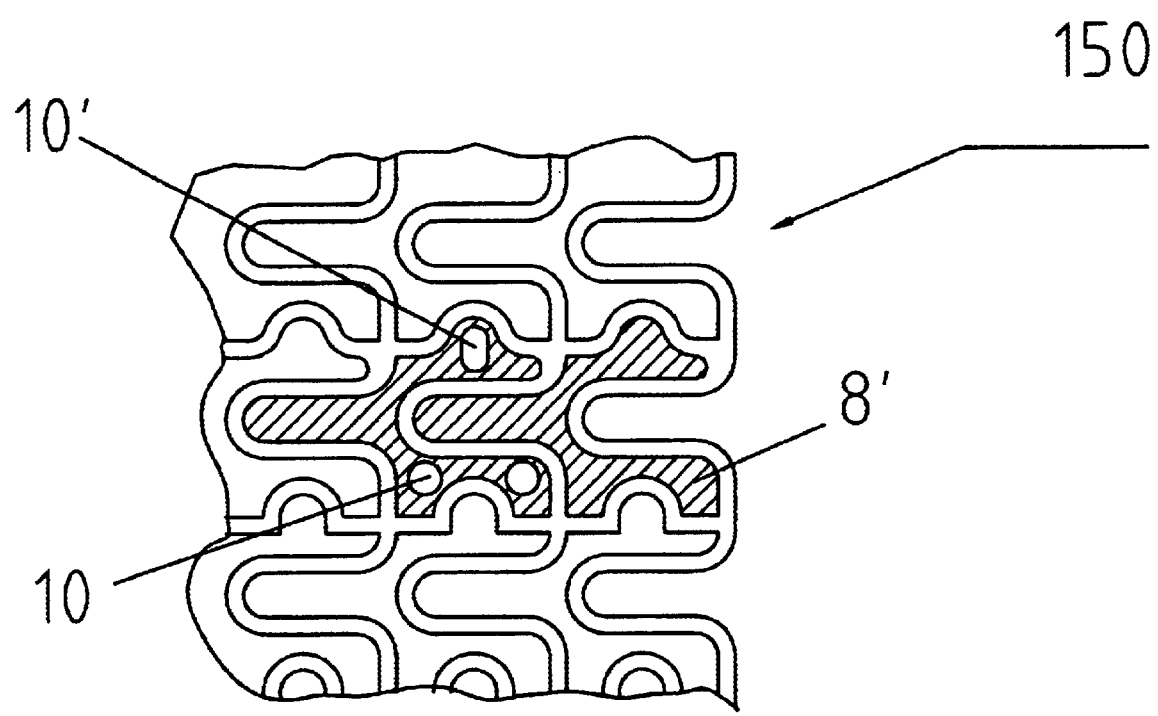
FIG. 3 is a schematic depicting the area of a metal blank that is removed to form the outline of a cathode used for making the stent in accordance with the present invention.

FIG. 3 shows an alternative process of forming the stent outline, for example, by drilling small holes 10 or by milling depressions 10' of various sizes. If the size of the stent pattern is very small it is possible to form raising regions 8', which are mirror representation of the stent outline.

Figure 4:
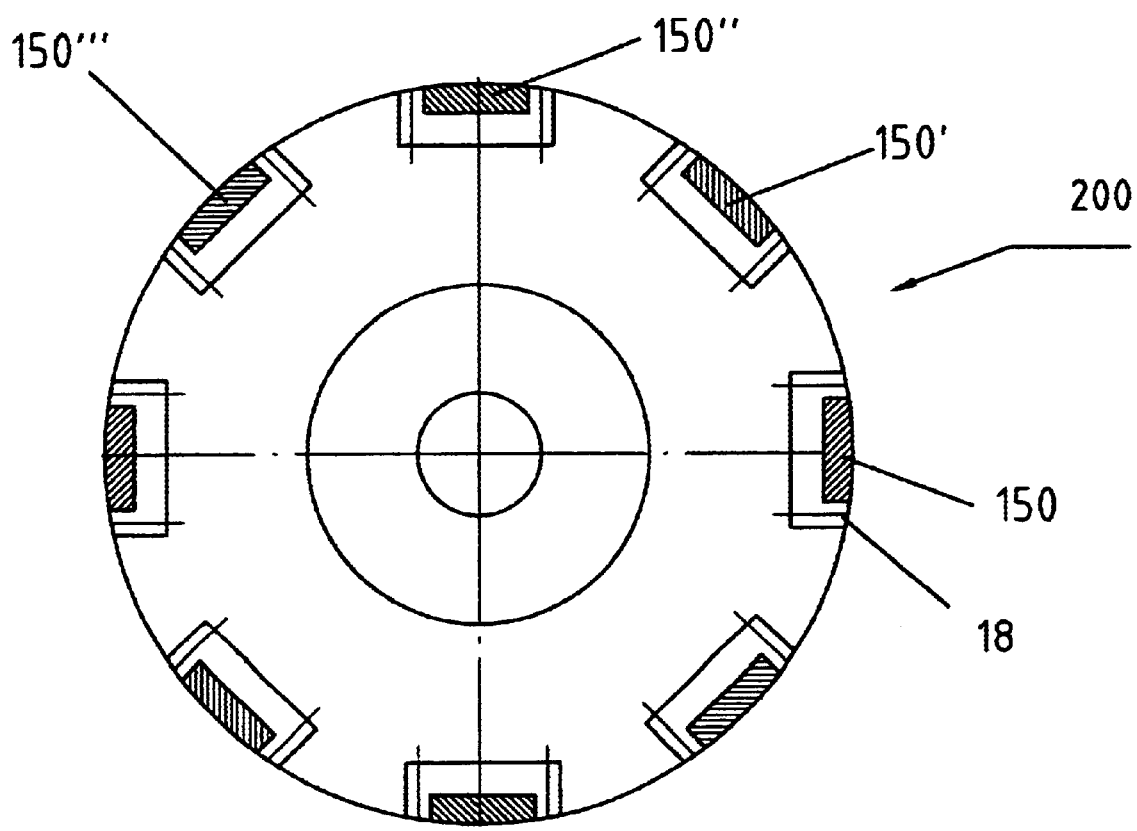
FIG. 4 is a schematic showing a rotator carrying multiple cathodes for manufacturing of stents of the same or different patterns in accordance with the present invention.

As shown on FIG. 4, once the cathode metal plate 150 is complete, it is mounted on the periphery of a rotator 200. Other cathode plates 150', 150" . . . 150$^n$, selected by a system operator, may also be placed on the rotator 200. Each cathode plate 150 . . . 150$^n$ may have the same or different stent pattern geometries. The cathode metal plate 150 is mounted tangentially to the rotator 200 such that the outline band pattern of the cathode metal plate 150 faces outward away from the center axis of the rotator 200. An insulating coating S (FIG. 6) is applied to the surface of the cathode metal plate 150 before mounting it on the rotator 200. The entire periphery of the rotator may then be ground, for example, on a circular grinding machine, as required, to remove excess insulating coating S and to ensure a uniform surface of each cathode. The insulating coatings, which can be used are known and need not be described herein.

FIG. 5 shows the top view of the cathode metal plate 150. Shorter length stents are formed by dividing the cathode metal plate 150 along the lines 3a–3b, 4a–4b, etc. (FIG. 1) using one of more of the prior art methods mentioned above. Each shorter section of stent is electrically insulated from the others. They are individually secured to an insulating base 18 by use of conductive fasteners 19, such as metal screws, which conduct current to that portion of the cathode metal plate 150. The entire cathode metal plate 150 is secured to the insulating base 18 by pins K and L which extend through contact base end areas A and B and provide the electrical contact for the cathode metal plate 150.

Also as shown in FIG. 5, only a portion of the cathode metal plate 150, with dimensions D×Lmax, contains the stent outline 9. The rest of the plate 150, with dimensions E×Lmax, is blank, except for the metal lead bands 14, 15, 16 and 17 (the number depending on the number of shorter stent lengths desired). These leads are formed in the same manner as the rest of the stent, using one or more of the prior art methods used to form stent outline 9. The lead bands initiate from slots 20 cut in the cathode plate 150 along lines 3a–3b, 4a–4b, etc. The slots are filled with electrically insulating material, e.g., self-hardening resin.

It will be explained further in more details that final cutting of the stent blank can be performed electrochemically by supplying current through slots 20 to the selected lead bands of the cathode plate. This is possible since each shorter length section of the cathode plate may have its own autonomous current supply.

Figure 6:
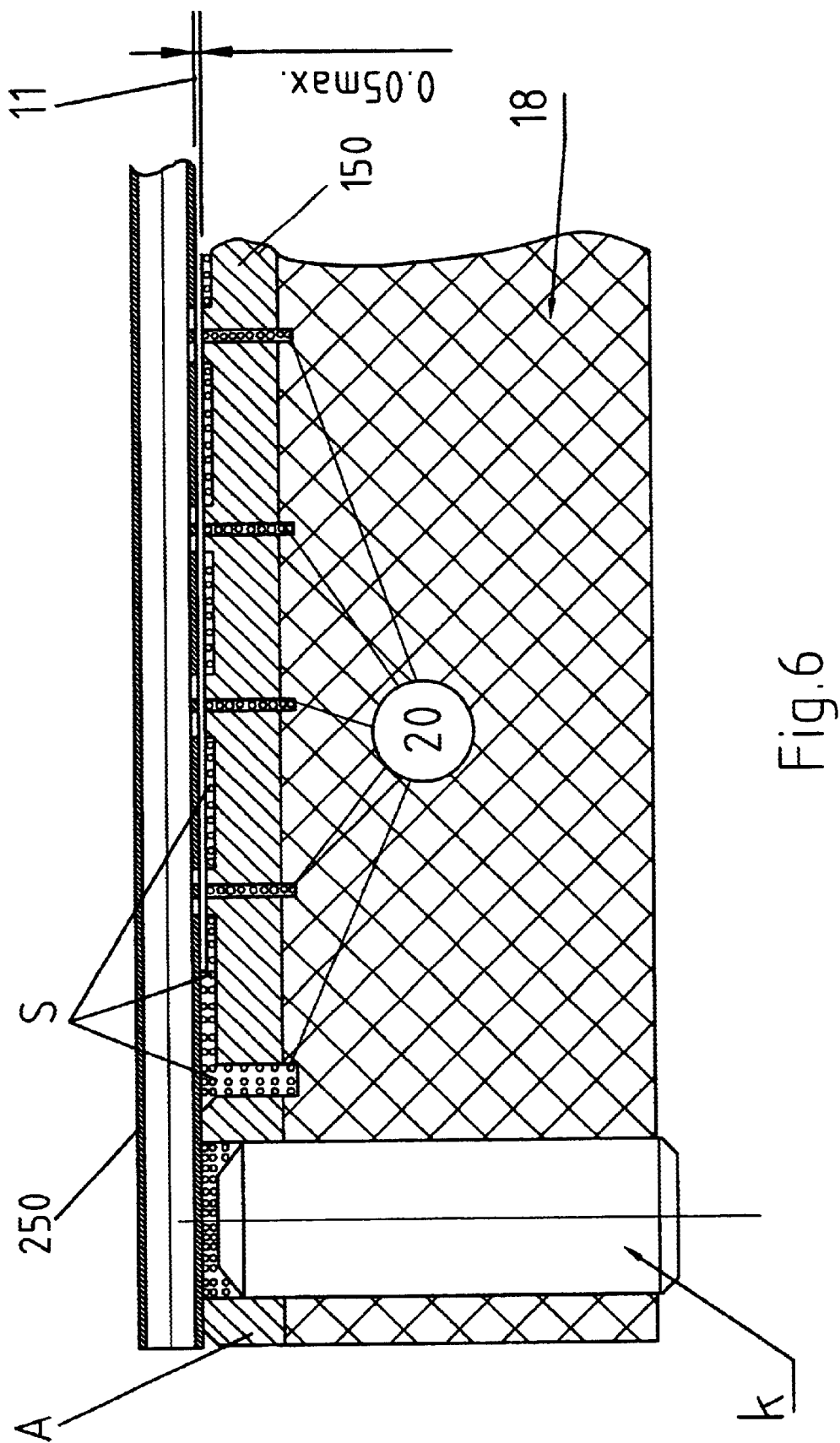
FIG. 6 is a partial cross-sectional view of the cathode depicted in FIG. 5.

FIG. 6 shows a partial cross-section of one-half of the cathode metal plate 150 cut at centerline O—O (FIG. 5). A thin pipe, called a stent blank 250, from which the stent 100 is formed, is placed on the surface of the cathode metal plate 150. The stent blank 250 is contained within a hollow mandrel, which is described in more detail below. The blank 250 is positioned within the mandrel in such a manner that it contacts the cathode at insulated base end areas A and B (FIG. 5). The rest of the blank is separated from the cathode stent outline 9 by space 11, which is approximately 0.05 mm. The distance separating the cathode metal plate 150 and the stent blank 250 depends on the specific electrolyte that will be used during stent processing and the current strength, but should be about 0.05 mm. To ensure proper spacing, insulating base end areas A and B are electrically monitored by supplying to them a weak current; the position of the stent blank 250 is adjusted according to the electrical signal received. FIG. 6 also shows how the slots 20 extend above the insulating base 18.

Figure 7:
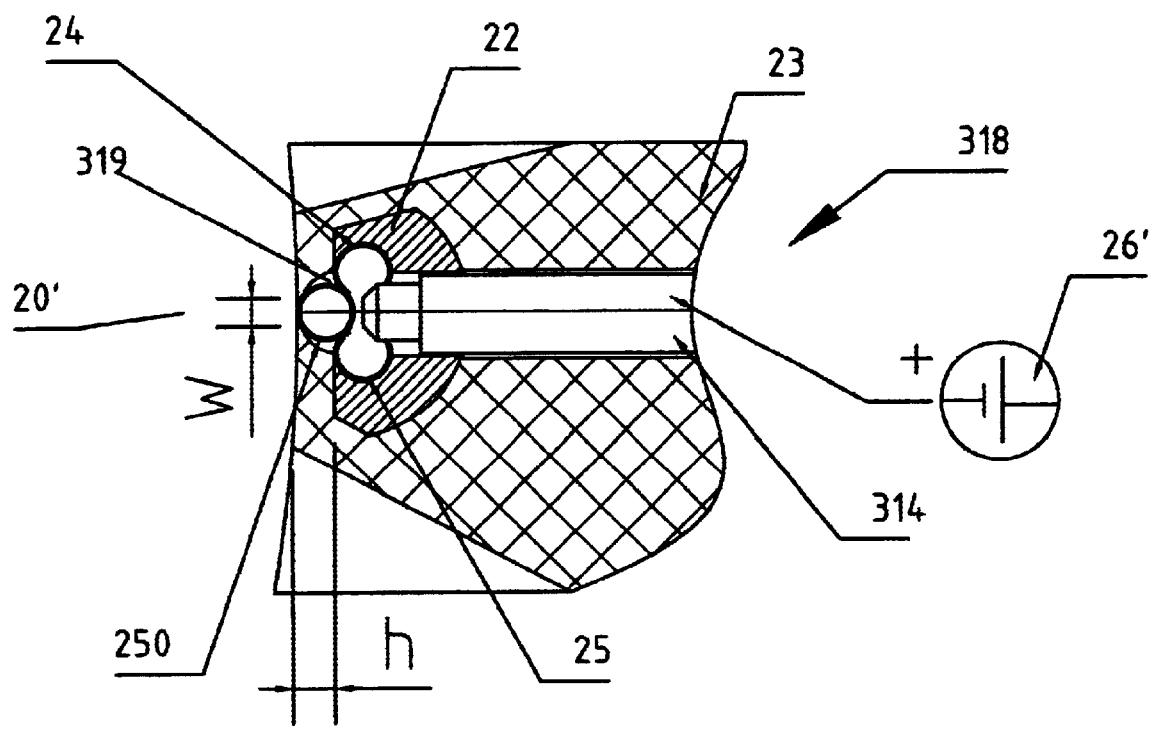
FIG. 7 is a cross-sectional view of the mandrel portion of the manufacturing apparatus of the present invention.
Figure 9:
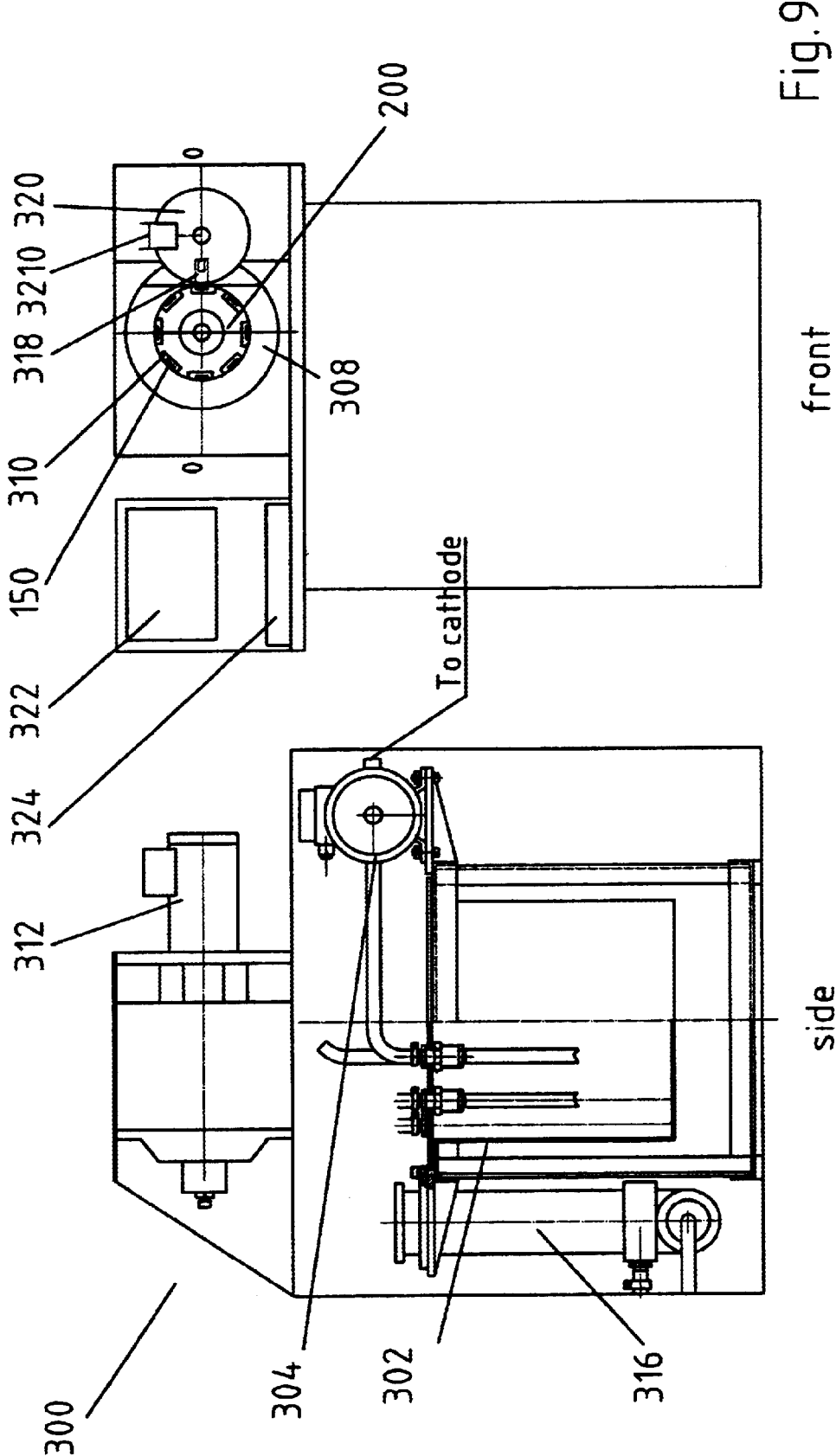
FIG. 9 is a side and end view of the manufacturing equipment of the present invention.

FIG. 7 shows the tubular stent blank 250 contained within a hollow mandrel 318 (FIG. 9). It should be understood that the rotator 200 (FIG. 4) is located to the left of the mandrel 318 adjacent the outwardly facing portion of the mandrel. It should also be appreciated that the rotator 200 carries cathode plates 150, 150', 150", etc., and one of the cathode plates is brought in the working position opposite the stent blank 250. The mandrel 318 contains a longitudinal slit 20' having width W. By virtue of this provision the electrochemical treatment is localized to the area exposed by the slit. The width W is determined by stent blank diameter, minimal inter-electrode clearance, possible non-linearity of the stent blank 250 and other factors.

The mandrel 318 includes an electrically non-conducting casing 23 which can be TEFLON® or any other conventional non-conductive material. A metal bushing 22 is positioned within casing 23. Casing 23 extends a distance h, which is about 0.1 to about 0.2 mm, beyond metal bushing 22. While this distance is not shown in the other drawings for simplicity purposes, it should be mentioned that a separation distance is provided to prevent contact between the metallic bushing 22 and the electrolyte and thus the condition where the metallic bushing 22 is worked out during the electrolytic process.

The stent blank 250 is inserted into a hole 319 formed in the metal bushing 22. Two metal rests 24 and 25 are tightly positioned into the hole 319 to support opposite sides of the blank. The restes are made with logitudinal cuts Q (FIG. 8) to provide elasticity and may be tubular (circular cross-sections), flat elastic springs, or other suitable devices for supporting the stent blank. Rests 24 and 25 press the stent blank 250 agaist the ligitudinal slit 20' to ensure that the blank is in contact with areas A and B of the cathod plate. At the same time, rests 24 and 25 supply electric power to the stent blank 250 from the positive pole of a power source 26' (FIG. 7) through one or more of screw 314 into the bushing 22. In this manner, electrical current is supplied to both sides of the tubular stent blank 250 simultaneously.

As soon as the stent blank 250 is properly mounted, forcible rotation of the blank and of the rotator begins. Both the rotator 200 (FIG. 4) and the stent blank 250 are simultaneously rotated by use of a drive and guide roller, as discussed below. By virtue of simultaneous rotation the blank revolves with respect to the cathode plate without slippage on areas A and B.

Figure 8:
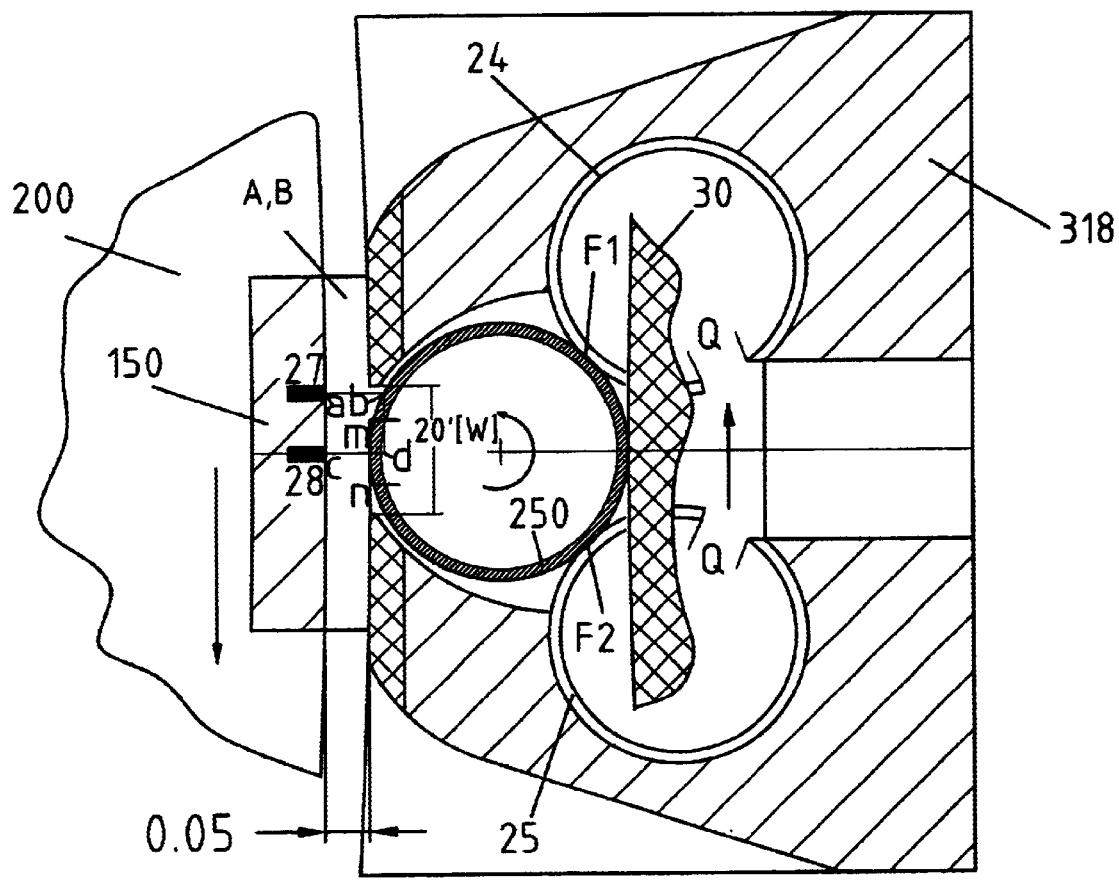
FIG. 8 is a detailed schematic of the cross-section view of FIG. 7.

FIG. 8 shows the stent blank 250 contained within the hollow mandrel 318 in contact with cathode plate end areas A and B. During processing, the rotator 200, with its attached cathode plate 150 and tubular blank 250, are rotated simultaneously in the direction shown by arrows, such that the stent blank 250 makes two consecutive revolutions. An electrolyte is supplied under pressure between the stent blank and cathode plate for electrochemical processing, as explained hereinafter in greater detail. During the first revolution the stent pattern (FIG. 1) is electrochemically formed. During the second revolution, current is supplied to those lead bands of the cathode plate, which define the required length of the stent and thus its lateral ends are electrochemically cut from the stent blank. Because processing is restricted to the narrow opening slit 20', a high current of about 50 A/cm$^2$ or greater can be used, the dynamic effect of electrolyte upon the stent blank 250 is minimized, and ionization scattering is reduced, thus minimizing distortion of the stent blank 250. Further, the distance between the cathode outline bands, 27,28, and the stent blank 250 is equal, that is, distance a–b is approximately the same as the distance c–d, as shown. This distance may be electrically monitored for precise control during fabrication of the stent 100. Monitoring this separation distance reduces the possibility of short circuits between the cathode metal plate 150 and stent blank 250.

Also as shown in FIG. 8, the slit 20' in the mandrel 318 restricts the emergence of the tubular stent blank 250 out of the mandrel 318 even where the stent blank 250 is substantially non-rectilinear. Similarly, in the course of the stent blank 250 processing, the slit prevents short circuits, which can reduce the cathode strength and rigidity. This would, therefore, prevent a decrease in the rigidity of the stent 100.

As previously mentioned, both the rotator 200 and the stent blank 250 rotate by use of a dedicated drive (not shown) and a guide roller 30. As shown in FIG. 8, displacement of stent blank 250 with respect to mandrel 318 is restricted by the cathode metal plate 150 at a line m–n between contact areas A and B, and at points of contact F1 and F2 between the stent blank and rests 24 and 25, respectively. Centerless rotation of the stent blank 250 is ensured by guide roller 30 driven by the drive, which rotates rotator 200. The centerless rotation of the stent blank 250 eliminates the need for additionally cleaning and processing the internal surface of the stent after electrochemical treatment.

Excess current load on stent bridges 7a,7b (FIG. 2), which may increase the temperature of the material at this location to an undesirable level, should be minimized. On the other hand, when stent processing begins, the maximum possible technological current can be supplied to the stent blank 250. A computer 322 (FIG. 9) is used to maintain the current density at a rated value based on the selected stent configuration and length parameters. During processing, as soon as the section of the stent blank 250 is reduced to the point where it is necessary to reduce the current, and, consequently, to decrease the metal removal rate, the computer 322 reduces the rate of angular motion of the blank 250 (that is, the rate of approach of points a–b). As a result, the radial feed decreases, thus reducing the current load on the stent bridges.

FIG. 9 shows the stent manufacturing apparatus 300. During processing, pump 304 delivers electrolyte from tank 302 to mandrel 318 and into the spacing between the cathode metal plate 150 and the stent blank 250 at a velocity of about 8 to about 10 m/s. Although weak electrolytes, such as, NaCl, NaNO$_3$, FeCl$_3$ solutions are preferred, other known electrolytes may be used. As a result, it is not necessary to use a cathode made from gold or platinum; rather, less expensive materials such as stainless steel, brass or other copper alloys may be used. Although not shown in FIG. 9, electrolyte conditioning means well known in the art may also be included.

Also shown in FIG. 9, the apparatus includes a insulation flange 308 on which rotator 200 is mounted with removable insertions 310 carrying cathode metal plates 150, 150' . . . 150$^n$ with outline patterns of various configurations. Also included are a rotation drive 312, electrolyte tank 302, pump 304, electrolyte filtration unit 316, mandrel 318, casing 320, with an opening 321 for reloading the mandrel 318, computer (conventional) 322 and interface board 324. Rotation drive 312 is capable of simultaneous rotating both the guide roller 30 and rotator 200. Mandrel 318 is mounted in the roller casing 320 through the opening 3210 when it is turned to a position parallel to the O—O centerline.

An operator must enter only two parameters into the digital computer 322 to produce a custom stent: the number of the cathode metal plate 150 (FIG. 5) on the rotator 200 (which identifies its position relative to the other cathodes and its particular outline pattern) and the required stent length. As mentioned above, the computer 322 monitors electrical current load to the stent blank 250 and electrolyte temperature. As material is removed from the stent blank 250 during operation, the computer 322 reduces the angular velocity of rotation of the stent blank 250 and decreases the current load on the stent blank 250 as the stent is being formed.

Figure 10:
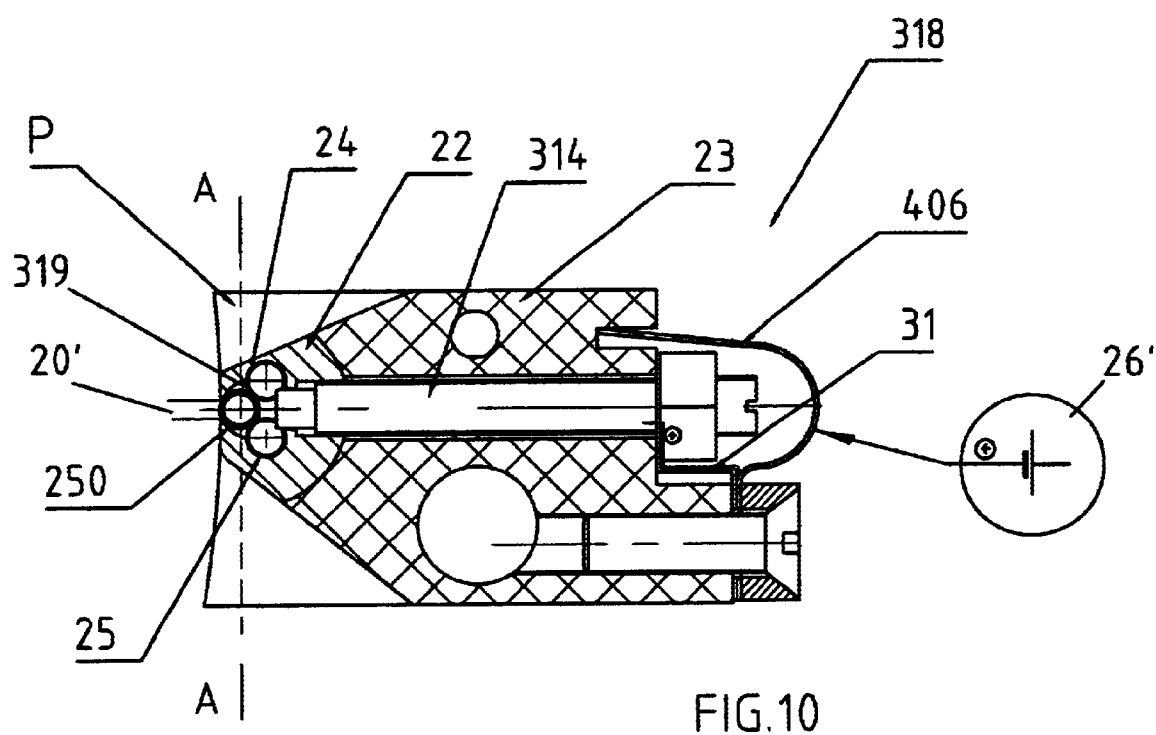
FIG. 10 is a broader cross-sectional view of the mandrel of FIG. 7.
Figure 11:
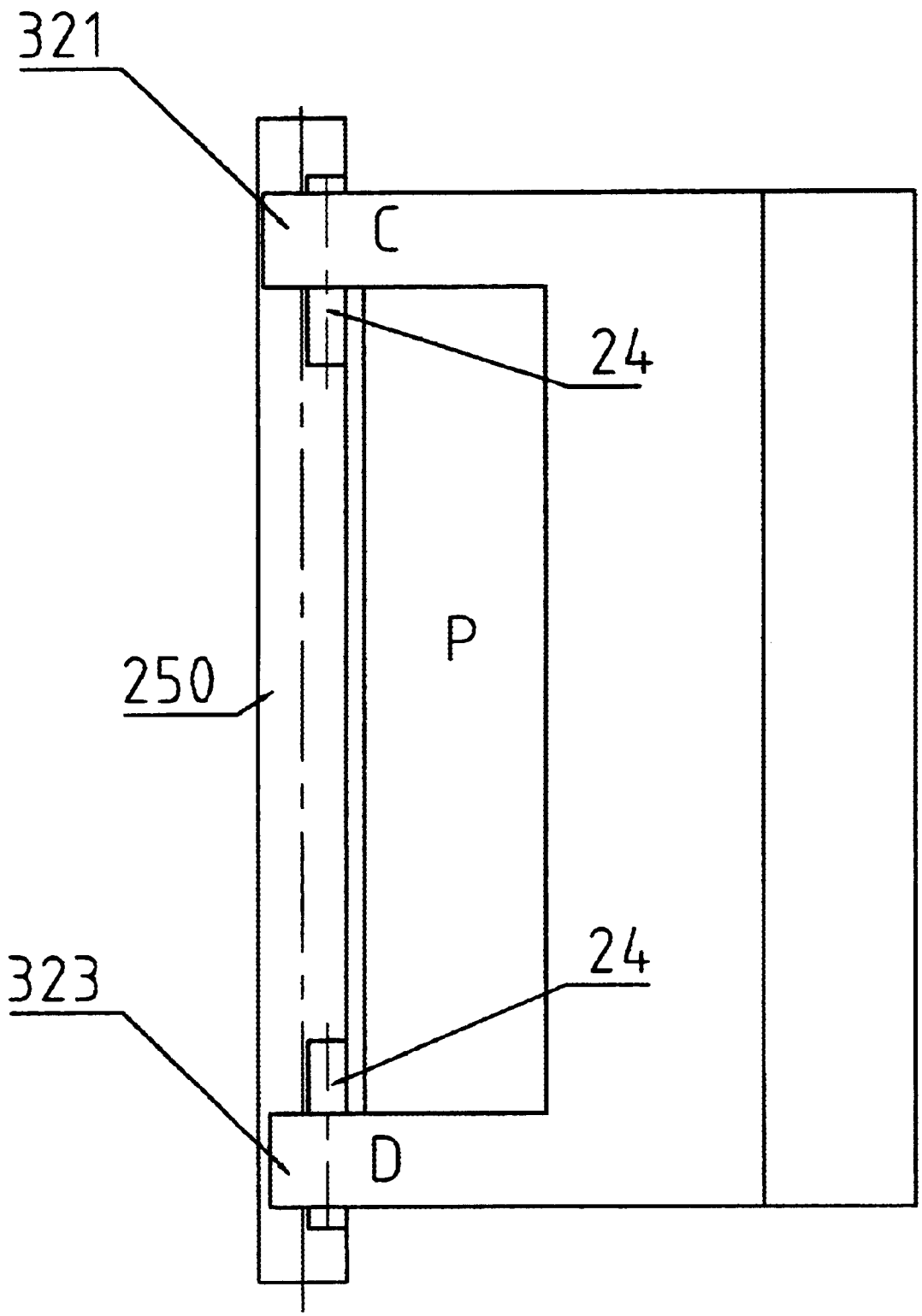
FIG. 11 is a plan-view (top) of the mandrel depicted in FIG. 7, FIG. 8 and FIG. 10.

FIG. 10 shows the mandrel 318 of the present invention in more detail. Prior to processing, the stent blank 250 is inserted into the hole 319 of metal bushing 22, which is part of the mandrel 318. Rigid spring 406 is provided for pressing mandrel 318 towards the cathode during operation. By virtue of this provision it is ensured that the blank always contacts cathode areas A and B. At the same time the spring is in electrical contact with a screw 314, which touches rests 24,25 and thus positive voltage can be supplied from the source 26' to the blank via screw 314 and rests 24,25. It is seen also in FIG. 10 that forward portion of the mandrel casing which faces the cathode is configured with a cavity P. Into this cavity electrolyte is pumped under pressure from the tank 302 for carrying out the electrochemical process. FIG. 11 shows a partial plan-view (top) of the mandrel 318. The stent blank 250 is mounted on rests 24 and 25 (FIG. 10), which were described above as two short metal tubes with longitudinal slits Q (FIG. 8). Rests 24, 25 are secured to the metal bushing 22 (FIG. 10). Ends 321, 323 of lateral surfaces C and D of the mandrel case are pressed against cathode metal plate contact areas A and B ensuring a constant inter-electrode clearance along the entire length of the stent blank 250 (FIGS. 5 and 8).

Figure 12:
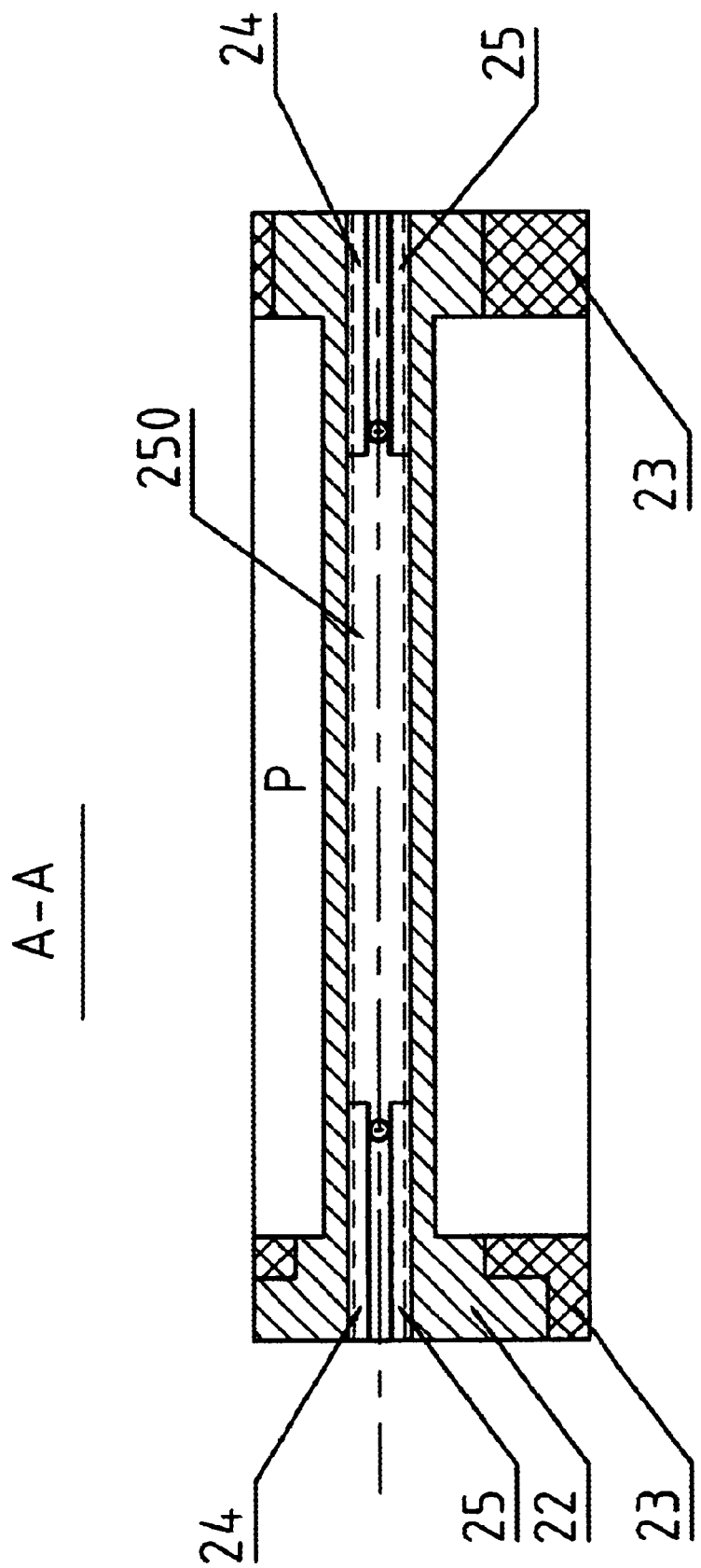
FIG. 12 is a cross-sectional view of the mandrel depicted in FIG. 10.

FIG. 12 shows a cross-section of the mandrel 318 at surface A–A (FIG. 10), showing the relative positions of the metal bushing 22, non-conductive casing 23, rests 24 and 25, stent blank 250 and cavity P.

Figure 13:
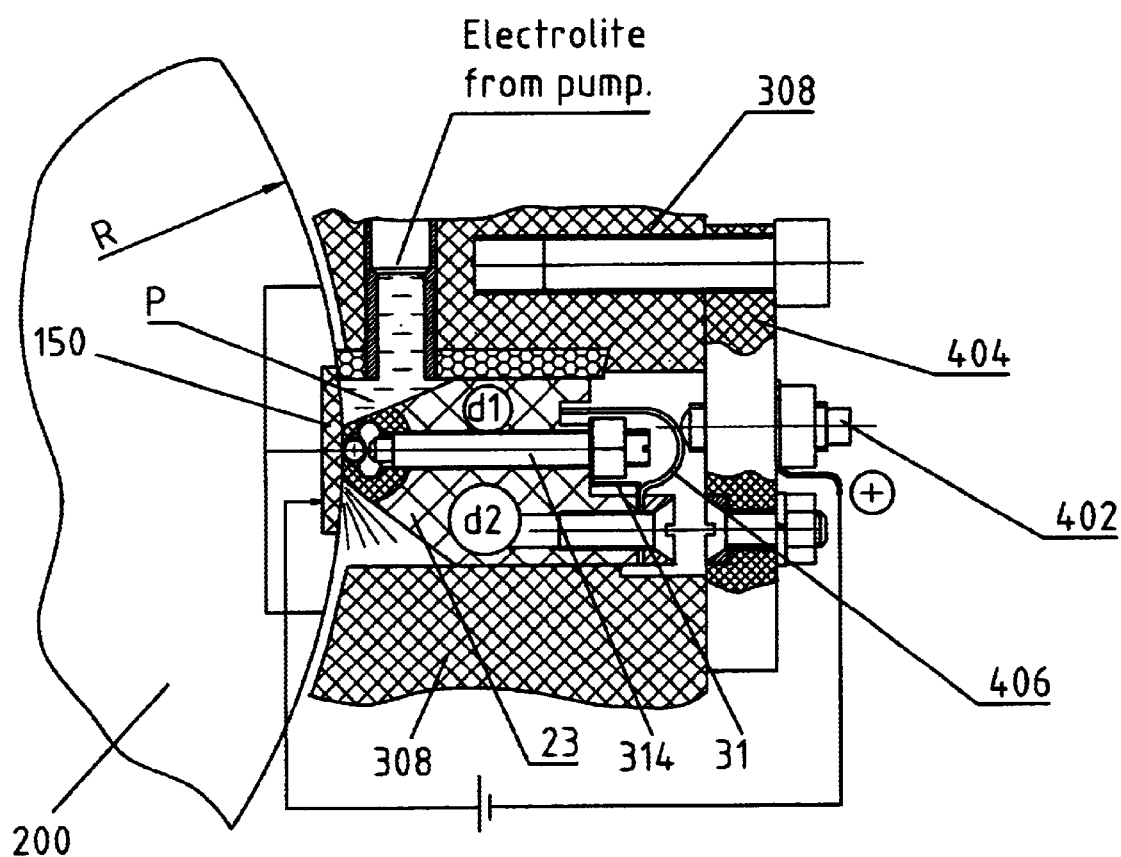
FIG. 13 is another cross-sectional view of a mandrel according to the present invention.

FIG. 13 shows a view of the mandrel 318 along with rotator 200. Prior to processing the stent blank 250, fingers of a robotic gripping device through openings d1 and d2 retain the mandrel 318, already loaded by the tubular stent blank 250. The robotic gripping device introduces the mandrel through opening 3210 into insulation flange 308 of the stent manufacturing apparatus 300. Screw 402 is secured over a fixed electro-insulated strip 404. Power is supplied through screw 402 and rigid spring 406, strip 404, screw 314 (FIG. 10) and lamella 31 to bushing 22 and through rests 24 and 25 (FIG. 10) to the stent blank 250. The casing of mandrel 318 is configured so that its cathode adjacent end has a radius, R, equal to the radius of the rotator 200. FIG. 13 also illustrates cavity P where electrolyte is introduced to enable establishing of electrochemical process between the cathode metal plate 150 (FIG. 4) and stent blank 250 (FIG. 10).

Figure 14:
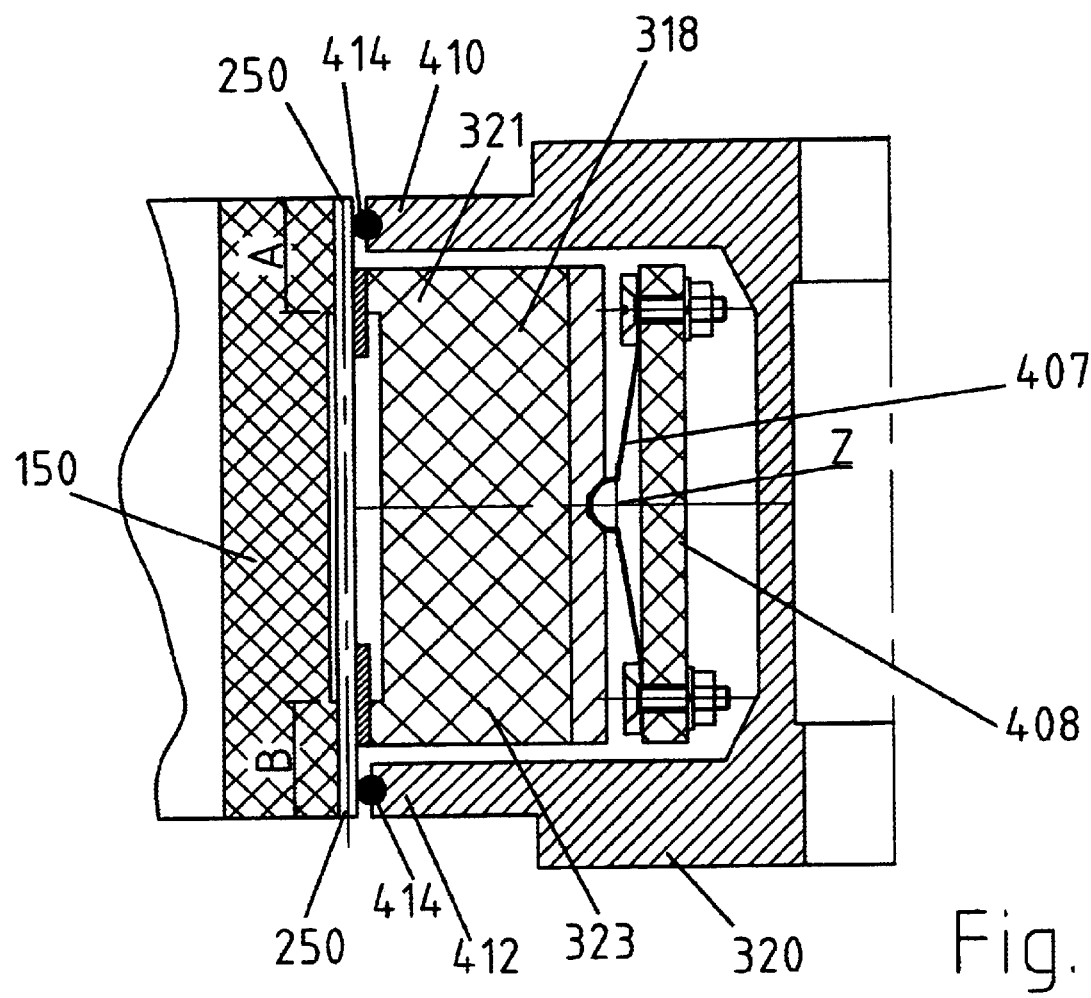
FIG. 14 is a cross-sectional view of the interface between the cathode of FIG. 4 and a mandrel according to the present invention.

FIG. 14 shows the mandrel 318 seated inside the hold-down roller casing 320. In this configuration, the mandrel is fixed by a flat semi-spherical spring 407 secured on stationary plate 408. This allows the mandrel 318 to self-align with respect to axis Z. Consequently, mandrel ends 321, 323 are forced against the cathode metal plate 150, regardless of the geometric irregularities of the stent blank 250 (e.g., non-linearity of the generating line, etc.). The ends 410, 412 of casing 320 are encircled by elastic friction binding bands 414 to provide for reliable rotation on two sides of the stent blank 250 when driven by roller 30. Additionally, longitudinal slit 20' provided in mandrel 318 restricts the hydrodynamic effect associated with electrolyte pressure on the stent blank 250. In this way, the electrochemical process is concentrated only in the area of slit 20'.

It is to be understood that the invention is not limited to the exact details of construction, operation, exact materials or embodiments shown and described, as obvious modifications and equivalents will be apparent to one skilled in the art. Accordingly, the invention is therefore to be limited only by the scope as set forth in the claims.

What is claimed:

1. Apparatus for electrochemically making stents from a tubular blank comprising:
    a rotator having cathodes thereon;
    a current source electrically connected to the cathodes;
    a source of electrolyte;
    means for pumping said electrolyte;
    means for controlling the electrochemical forming operation and
    a mandrel, positioned parallel to a rotational axis of said rotator, for holding said blank; said mandrel being made hollow and including a longitudinal slit for supplying electrolyte to the blank; said blank being positioned inside said mandrel.

2. The apparatus according to claim 1, wherein said mandrel is made with two supporting surfaces matching to a radius of the rotator.

3. The apparatus according to claim 2, wherein inter-electrode clearance is provided, said mandrel being made self-aligned with respect to a working cathode, employed for electrochemical forming operation to provide reliable adjacency of the blank to the corresponding cathode surfaces.

4. A method of manufacturing expandable stents for implanting into a body lumen, comprising the steps of:
    electrochemically forming said expandable stent just prior to implantation, said electrochemical forming including:
        providing a working cathode which includes a desired pattern for producing the stent;
        providing a tubular blank adjacent to said working cathode;
        delivering an electrolyte between said working cathode and said tubular blank: relative displacing said tubular blank and said working cathode; and,
        electrochemically producing the stent with said desired pattern,
    wherein a mandrel is used for receiving said tubular blank, said mandrel having a linear slit along its longitudinal length parallel to said tubular blank for introducing the electrolyte and wherein said linear slit is narrower than the diameter of said tubular blank.

5. The method of claim 4, wherein said tubular blank has a diameter and thickness equal to the stent to be manufactured.

6. The method of claim 5, wherein the ends of said tubular blank are cut after the stent is formed, said method for forming a finished stent taking less than about 30 minutes.

7. The method of claim 6, wherein the ends of said tubular blank are cut after the stent is formed, said method for forming a finished stent taking less than about 15 minutes.

8. The method of claim 4, further including the step of removing an insulating coating on said cathode before electrochemically forming the stent.

9. The method of claim 4, further including the step of customizing a size and shape of said expandable stent to be in accordance with a patient's anatomy.

10. The method of claim 9, further including the step of implanting said stent into the body lumen.

11. The method of claim 4, wherein said electrochemical forming employs a current density of about 50 $A/cm^2$, or more.

12. The method of claim 4, wherein said electrolyte is delivered at a velocity of from 8 m/s to 10 m/s.

13. The method of claim 4, wherein said tubular blank is displaced by centerless rotation.

14. A method of custom-forming an expandable stent in an operating or emergency room for implanting the stent into a body lumen of a patient, comprising the steps of:
    providing a plurality of cathodes, at least some of which includes a different stent pattern on a rotator;
    providing a plurality of tubular blanks, at least some of which include a different material, diameter and thickness;
    selecting a working cathode from said plurality of cathodes with desired stent pattern;
    selecting a stent blank from said plurality of tubular blanks; mounting said stent blank in an operative relationship to said working cathode; rotating said rotator while delivering an electrolyte between said working cathode and said stent blank to electrochemically form the stent having the desired stent pattern; and recovering and preparing the stent for implantation into the patient's body lumen.

15. The method of claim 14, further including a mandrel for receiving said stent blank, said mandrel having a linear slit along its longitudinal length parallel to said stent blank for introducing the electrolyte and wherein said linear slit is narrower than the diameter of said stent blank.

16. The method of claim 14, further including the step of removing an insulating coating on said plurality of cathodes before electrochemically forming the stent.

17. The method of claim 14, wherein said electrochemical forming occurs at a current density of about 50 A/cm$^2$, or more.

18. The method of claim 14, further including the step of cutting the ends of said electrochemically-formed stent.

19. The method of claim 14, wherein said electrolyte is delivered at a velocity of from 8 m/s to 10 m/s.

20. The method of claim 14, wherein said tubular blank is rotated by centerless rotation.

21. An apparatus for custom-forming an expandable stent in an operating or emergency room during a procedure to implant the stent into a body lumen of a patient for implantation into a body lumen, comprising:

a rotator, for carrying one or more cathodes;

a mandrel positioned parallel to a rotational axis of said rotator, for holding a tubular blank in operative relationship to a working cathode, selected from said one or more cathodes;

a conduit for delivering electrolyte to a working cathode and said tubular blank; means for simultaneously rotating said rotator and said tubular blank; and means for supplying electrical voltage to the working cathode and to said tubular blank to produce a stent.

22. The apparatus of claim 21, wherein said working cathode and said tubular blank are separated by a distance not more than 0.05 mm.

23. The apparatus of claim 21, wherein said mandrel includes a linear slit directed parallel to the length of said tubular blank for delivering said electrolyte between the working cathode and the tubular blank and wherein said linear slit is narrower than the diameter of said tubular blank.

24. The apparatus of claim 21, wherein said one or more cathodes is made from a metal selected from the group consisting of gold, platinum, stainless steel, brass, copper, or alloys thereof.

25. The apparatus of claim 21, wherein said tubular blank has a diameter and thickness equal to said stent.

26. The apparatus of claim 21, further comprising a housing for containing therein said mandrel, said rotator, said tubular blank, said one or more cathodes, and said conduit and wherein said housing is positionable in an area substantially near a patient being treated for a stent implant.

27. The apparatus of claim 21, wherein said mandrel includes a lateral support comprising two pairs of tubular rests, each of which includes a longitudinal slit, for supporting said tubular blank in said mandrel in operative relationship to the working cathode.

28. The apparatus of claim 21, wherein said mandrel is in a self-aligning relationship to the working cathode.

29. A method of manufacturing expandable medical stents for implantation into blood and urological vessels of a patient, comprising the steps of:

determining a configuration and size of a stent to be implanted;

electrochemically forming said stent from a tubular blank during a procedure to implant the stent, said electrochemically forming comprises relative displacing of a working cathode provided with a desired pattern and the tubular blank while delivering an electrolyte between the working cathode and the tubular blank, and implanting said stent into said patient, wherein said step of electrochemically forming comprises cutting the blank to a preset length in one operation using a cathode multiple tool, which together with the tubular blank, is rotated.

30. The method according to claim 29, in which said electrolyte is delivered to an external surface of the blank.

31. The method according to claim 30, in which said relative displacing is carried out by a centerless rotation of the blank and said electrochemically forming comprises supplying electrical current to the blank simultaneously with its rotation.

32. The method according to claim 31, wherein operating par parameters of said electrolyte, condition of the working cathode and cross-section of the stent, are automatically controlled.

33. An apparatus for custom-forming an expandable stent in an operating or emergency room during a procedure to implant the stent into a body lumen of a patient for implantation into a body lumen, comprising:

a rotator, for carrying one or more cathodes;

a mandrel positioned parallel to a rotational axis of said rotator, for holding a tubular blank in operative relationship to a working cathode, selected from said one or more cathodes;

a conduit for delivering electrolyte to the working cathode and said tubular blank;

means for simultaneously rotating said rotator and said tubular blank; and means for supplying electrical voltage to the working cathode and to said tubular blank to produce a stent.

34. The apparatus of claim 33, wherein said working cathode and said tubular blank are separated by a distance not more than 0.05 mm.

35. The apparatus of claim 33, wherein said mandrel includes a linear slit directed parallel to the length of said tubular blank for the delivery of said electrolyte between the working cathode and the tubular blank and wherein said linear slit is narrower than the diameter of said tubular blank.

36. The apparatus of claim 33, wherein said one or more cathodes is made from a metal selected from the group consisting of gold, platinum, stainless steel, brass, copper and alloys thereof.

37. The apparatus of claim 33, wherein said tubular blank has a diameter and thickness equal to said stent.

38. The apparatus of claim 33, further comprising a housing for containing therein said mandrel, said rotator, said tubular blank, said one or more cathodes, and said conduit and wherein said housing is positionable in an area substantially near a patient being treated for a stent implant.

39. The apparatus of claim 33, wherein said mandrel includes a lateral support comprising two pairs of tubular rests, each of which includes a longitudinal slit, for supporting said tubular blank in said mandrel in operative relationship to the working cathode.

40. The apparatus of claims 33, wherein said mandrel is in a self-aligning relationship to the working cathode.

* * * * *